US005580544A

United States Patent [19]
Dao et al.

[11] Patent Number: 5,580,544
[45] Date of Patent: Dec. 3, 1996

[54] PASTE FORMULATION USEFUL FOR SEED TREATMENT AND FOLIAR TREATMENT OF PLANTS

[75] Inventors: Dong C. Dao, Guelph; William L. Hallatt, Heidelberg; Heather L. Hibbett, Stoney Creek; Colin H. Drennan, Guelph, all of Canada

[73] Assignees: Uniroyal Chemical Company, Inc., Middlebury, Conn.; Uniroyal Chemical Ltd/Ltee, Elmira, Canada

[21] Appl. No.: 412,632

[22] Filed: Mar. 29, 1995

[51] Int. Cl.$^6$ .......................... A01N 25/02; A01N 25/24
[52] U.S. Cl. .......................... 424/43; 424/409; 424/715
[58] Field of Search .......................... 424/409, 715, 424/43

[56] References Cited

U.S. PATENT DOCUMENTS

| | | |
|---|---|---|
| 4,182,716 | 1/1980 | Znotins et al. |
| 4,319,033 | 3/1982 | Tsai et al. |
| 4,497,646 | 2/1985 | Rubio |
| 4,569,690 | 2/1986 | Brouwer et al. |
| 4,839,349 | 6/1989 | Covey et al. |
| 4,857,649 | 8/1989 | Lai et al. |
| 4,927,451 | 5/1990 | Brouwer et al. |
| 4,943,309 | 7/1990 | Bell |
| 4,945,113 | 7/1990 | Nowakowski et al. |
| 4,950,671 | 8/1990 | Lai et al. |
| 4,966,910 | 10/1990 | Lai et al. |
| 4,966,912 | 10/1990 | Relyea et al. |
| 4,979,982 | 12/1990 | Brouwer et al. |
| 4,981,508 | 1/1991 | Strunk et al. |
| 5,010,068 | 4/1991 | Dekeyser et al. |
| 5,039,332 | 8/1991 | Friedlander et al. |
| 5,061,716 | 10/1991 | Relyea et al. |
| 5,070,211 | 12/1991 | Dekeyser et al. |
| 5,071,862 | 12/1991 | Friedlander et al. |
| 5,080,226 | 1/1992 | Hodakowski et al. |
| 5,094,853 | 3/1992 | Hagarty |
| 5,114,464 | 5/1992 | Davis et al. |
| 5,134,133 | 7/1992 | Covey et al. |
| 5,134,144 | 7/1992 | Brouwer et al. |
| 5,134,145 | 7/1992 | Brouwer et al. |
| 5,139,152 | 8/1992 | Hodakowski et al. |
| 5,169,430 | 12/1992 | Strunk et al. |
| 5,176,735 | 1/1993 | Bell |
| 5,215,747 | 6/1993 | Hairston et al. |
| 5,222,595 | 6/1993 | Gouge et al. |
| 5,232,701 | 8/1993 | Ogawa et al. |
| 5,248,038 | 9/1993 | Hodakowski et al. |
| 5,253,759 | 10/1993 | Gouge et al. |
| 5,268,389 | 12/1993 | Harrison et al. |
| 5,319,102 | 6/1994 | Davis et al. |
| 5,328,942 | 7/1994 | Akhtar et al. |
| 5,346,704 | 9/1995 | Lajoie .......................... 424/409 |
| 5,464,627 | 11/1995 | Fu et al. .......................... 424/409 |

FOREIGN PATENT DOCUMENTS

| | | |
|---|---|---|
| 28484 | 11/1992 | Australia . |
| 2023547 | 8/1991 | Canada . |
| 2083468 | 5/1993 | Canada . |
| 221630A1 | 5/1985 | Germany . |
| 4273802 | 9/1992 | Japan . |
| 4297404 | 10/1992 | Japan . |
| 5017309 | 1/1993 | Japan . |
| 6001717 | 1/1994 | Japan . |
| 2095115 | 9/1982 | United Kingdom . |

OTHER PUBLICATIONS

Encyclopedia of Chemical Technology, Kirk–Othmer, Third Edition, vol. 7, John Wiley & Sons, Inc., 1979, pp. 430–447.
Encyclopedia of Chemical Technology, Kirk–Othmer, Third Edition, vol. 10, John Wiley & Sons, Inc., 1980, p. 232.
Encyclopedia of Chemical Technology, Kirk–Othmer, Third Edition, vol. 20, John Wiley & Sons, Inc., 1982, pp. 207–230.
McCutcheon's, vol. 1: Emulsifiers & Detergents, 1994 North American Edition, McCutcheon Division, McPublishing Co., pp. 287–310.
McCutcheon's vol. 1: Emulsifiers & Detergents, 1994 International Edition, McCutcheon Division, McPublishing Co., pp. 257–280.
McCutcheon's vol. 2: Functional Materials, 1994 North American Edition, McCutcheon Division, The Manufacturing Confectioner Publishing Co., pp. 122–142.
McCutcheon's vol. 2: Functional Materials, 1994 International Division, McCutcheon Division, McPublishing Co., pp. 47–56.

*Primary Examiner*—Peter F. Kulkosky
*Attorney, Agent, or Firm*—Daniel Reitenbach

[57] ABSTRACT

Water-dispersible paste formulations used in connection with seed treatment and foliar treatment of plants provide excellent dust and rub-off control. The paste formulations comprise an active ingredient and a hydrocarbon oil carrier having a boiling point of at least 150° C. The carrier is present in an amount that is effective for reducing dusting off of the plant leaf or seed. The paste formulations further include a surfactant and an effervescent comprising an alkaline carbonate and a solid and weak acid. The surfactant, the alkaline carbonate, and the solid and weak acid are respectively present in an amount that is effective for enabling the paste formulation to readily and quickly be dispersed in water. The paste formulations are especially suitable for containment in water soluble and/or water-dispersible bags or pouches, such use tending to render the active ingredient safer to handle and therefore better for consumers and the environment.

23 Claims, No Drawings

PASTE FORMULATION USEFUL FOR SEED TREATMENT AND FOLIAR TREATMENT OF PLANTS

TECHNICAL FIELD

Our present invention, in general, is directed to water-dispersible paste formulations used for treating seeds. Additionally, our invention is generally directed to water-dispersible paste formulations used for foliar treatment of plants.

More particularly, our invention is directed to water-dispersible paste formulations, used for treating seeds and for foliar treatment of plants, wherein the paste formulations are able to be contained within such water-soluble or water-dispersible containers as water-soluble or water-dispersible bags and pouches.

BACKGROUND ART

Compositions and formulations used for treating seeds and for foliar treatment of plants are well known.

In this regard U.S. Pat. No. 5,328,942 to Akhtar et al. as well as United Kingdom Patent Application GB 2 095 115 A to Cannan et al. of FMC Corporation are illustrative.

Formulations used for treating seeds and for foliar treatment of plants and contained within water-soluble or water-dispersible containers such as water-soluble or water-dispersible bags or pouches are also well known.

U.S. Pat. Nos. 5,222,595 and 5,253,759 (both to Gouge et al.) and U.S. Pat. Nos. 5,080,226; 5,139,152 and 5,248,038 (all to Hodakowski et al.) are illustrative in this regard.

To reduce costs, many seed-treatment and foliar-treatment formulators would prefer to be able to use paste formulations instead of conventional, commercially-available liquid formulations, wherein such use of paste formulations results in significant cost savings.

When using water-soluble containers it is highly desirable, of course, that contained formulations include as little water as possible.

While the utilization of a paste formulation tends to result in lesser included amounts of water, a paste formulation tends to disperse slowly.

Yet, it is highly desirable that formulations for treatment of seeds as well as formulations for foliar treatment of plants readily and quickly disperse, preferably uniformly, when combined with water.

Those skilled in the relevant art know, however, that conventional non-aqueous paste formulations are generally not capable of readily and quickly dispersing.

Furthermore, and as those in the relevant art also know full well, the selection of a dispersant or dispersing agent for inclusion in a paste formulation for treatment of seeds or for foliar treatment of plants must be done carefully for several reasons.

For example, while a dispersant, in general, may typically be selected for purposes of providing a certain formulation with a number of desired physical properties, some of which are mentioned herein, the presence of a dispersant or dispersing agent in the paste formulation —because of the surface-charge nature of the dispersant or dispersing agent— may undesirably affect the ability of the formulation to adhere to (i.e. "stick to") a particular seed or plant leaf; and, if the formulation further includes a dye or coloring agent, may undesirably affect the ability of the formulation to uniformly color the seed or leaf that is to be treated.

It would therefore be desirable to have commercially-available a paste formulation which is not only able to disperse readily and quickly in water but which is also able to strongly adhere to and uniformly coat a treated seed or plant leaf.

Put simply, seed-treatment as well as foliar-treatment formulators would mandate a uniform coating of "actives" and coloring agent (if used) on their seed and leaves, wherein the seed-treatment and foliar-treatment coating neither "dusts" (i.e. neither causes formation of dust or other particles) nor rubs off their seed or leaves, neither of which is desirable.

Furthermore, the temperature of the water into which the paste formulation is to be dispersed can be an important consideration.

For example, because certain paste formulations will disperse acceptably in room temperature water, those skilled in the art would perhaps encourage use of warm water to achieve quicker, more uniform dispersion of a particular paste formulation.

A number of conventional seed-treatment and foliar-treatment formulations, however, are sold to applicators who combine the seed-treatment and/or foliar-treatment formulations with water "in the field," generally at times of the year when only cold water is available.

Those skilled in the relevant art can, of course, well appreciate that certain problems come to light when attempts are made to dissolve paste-containing water-soluble bags or pouches in cold water.

It would thus be desirable that there be available in the marketplace a paste formulation—such as for treatment of seeds or foliar treatment of plants—wherein the formulation is able to readily and quickly disperse, preferably uniformly, when combined with cold water.

The foregoing desiderata, as well as other features and advantages of our present invention will become increasingly more readily apparent to those skilled in the relevant art upon reading the following summary and detailed description of our present invention.

SUMMARY DISCLOSURE OF INVENTION

Water-dispersible paste formulations disclosed herein and used in connection with seed treatment and foliar treatment of plants have been found to provide excellent dust control and rub-off control.

Our novel paste formulations comprise an "active" agent or ingredient as well as a "sticker" agent or ingredient such as a hydrocarbon oil having a boiling point ("b.p.") of at least 150 degrees Celsius ("° C."), wherein the "sticker" agent or ingredient functions as a carrier and is present in an amount that is effective for reducing dusting off of the plant leaf or seed.

Preferably, the hydrocarbon oil has a b.p. of at least 200° C.

More preferably, the hydrocarbon oil has a b.p. of at least 220° C.

Our novel paste formulations further include a surfactant and an effervescent comprising an alkaline carbonate and a solid and weak acid, wherein the surfactant, the alkaline carbonate, and the solid and weak acid are respectively present in an amount that is effective for enabling the paste formulation to readily and quickly be dispersed in water, such as room temperature water, but especially in cold water.

The alkaline carbonate can be derived from an alkali metal (especially sodium or potassium), or from an alkaline-earth metal (especially calcium or magnesium), or from an ammonium or organoammonium group or cation (carbonate derived from a primary, secondary or tertiary amine, or from a quaternary ammonium cation), but is preferably derived from an alkali metal, especially sodium or potassium.

The solid and weak acid is advantageously either a carboxylic or polycarboxylic acid, or a phosphoric or phosphonic acid, or one of their salts or esters containing an acidic functional group.

Our novel paste formulations further include a dessicant or drying agent, an optional ingredient, to maintain the activity of the effervescent.

Our novel paste formulation may further include such additional optional ingredients as a foam-control agent or ingredient, a dispersant, a packaging-film agent or ingredient, a pigment agent or ingredient (also called a dye), and/or an anticaking agent or ingredient.

In particular, and as a result of our present invention, those paste formulations which are illustrative of our invention and further include a dye or other coloring agent or ingredient have been found to provide treated seed with excellent uniform-color control.

Furthermore, the pastes of our present invention are especially suitable for containment in water-soluble and/or water-dispersible bags, such use tending to render the active agent safer to handle and therefore better for consumers and the environment.

BEST MODE FOR CARRYING OUT THE INVENTION

Our present invention is susceptible to embodiment in various forms. We have accordingly described our invention with respect to a number of examples which embody various principles of our invention.

It is thus our intent that this disclosure be considered merely illustrative of our invention without limitation to the specific embodiments or examples discussed and described in detail herein.

In the following detailed description, certain terms will be utilized for purposes of conciseness and otherwise to elucidate the various aspects, features and advantages of our present invention. These terms are defined hereinbelow.

The term "active" as used herein shall, in general, be understood to mean any ingredient that is chemically active and/or biologically active in origin. In this regard an "active" ingredient can be a single ingredient or a combination of ingredients; and the meaning of the term "active" shall be understood to include but not be limited to the following:

(1) such arthropodicidally-active compositions-of-matter as are disclosed and listed in U.S. Pat. No. 5,093,853 (to Hagarty);

(2) such bactericidally-active compositions-of-matter as are disclosed in U.S. Pat. No. 4,182,716 (to Znotins et al.);

(3) such fungicidally-active compositions-of-matter as are disclosed in U.S. Pat. No. 4,182,716 (to Znotins et al.); U.S. Pat. No. 4,497,646 (to Rubio); U.S. Pat. No. 4,569,690 (to Brouwer et al.); U.S. Pat. Nos. 4,857,649 and 4,950,671 (both to Lai et al.); U.S. Pat. Nos. 4,966,912 and 5,061,716 (both to Relyea et al.); U.S. Pat. Nos. 5,039,332 and 5,071,862 (both to Friedlander et al.); and U.S. Pat. No. 5,215,747 (to Hairston et al.);

(4) such herbicidally-active compositions-of-matter as those disclosed in U.S. Pat. No. 4,497,646 (to Rubio); U.S. Pat. Nos. 4,569,690 and 4,927,451 (both to Brouwer et al.); U.S. Pat. No. 4,945,113 (to Nowakowski et al.); U.S. Pat. No. 4,966,910 (to Lai et al.); U.S. Pat. No. 4,979,982 (to Brouwer et al.); U.S. Pat. No. 4,981,508 (to Strunk et al.); U.S. Pat. No. 5,114,464 (to Davis et al.); U.S. Pat. No. 5,169,430 (to Strunk et al.); and U.S. Pat. No. 5,319,102 (to Davis et al.);

(5) such microbiologically-active compositions-of-matter as are disclosed in U.S. Pat. No. 5,215,747 (to Hairston et al.);

(6) such pesticidally-active compositions-of-matter as those disclosed in U.S. Pat. No. 4,839,349 (to Covey et al.); U.S. Pat. No. 5,010,068 (to Dekeyser et al.); U.S. Pat. No. 5,134,133 (to Covey et al.); and U.S. Pat. Nos. 5,134,144 and 5,134,145 (both to Brouwer et al.); and (7) such plant growth regulant-active compositions-of-matter as those disclosed in U.S. Pat. No. 4,319,033 (to Tsai et al.); U.S. Pat. No. 4,857,649 (to Lai et al.); U.S. Pat. No. 4,943,309 (to Bell); U.S. Pat. No. 5,039,332 (to Friedlander et al.); U.S. Pat. No. 5,070,211 (to Dekeyser et al.); and U.S. Pat. No. 5,176,735 (to Bell).

Other "active" ingredients useful in conjunction with our present invention are cited and otherwise set forth in the examples of this patent specification.

The term "anticaking agent" shall, in general, be understood to mean a substance used to improve the integrity of a paste and to lessen the likelihood of settling of a suspension. The term "anticaking agent" shall, more particularly, be understood to mean a substance which promotes overall structure, body or suspension properties, or which provides a rheological modification to the final desired product.

The term "coating," which includes the term "film," as used herein means a composition-of-matter which adheres to, or covers, or is spread over a surface, wherein the term "surface" is referred to herein in its more general sense, namely, as a substrate.

The term "cold water" shall, in general, be understood to mean water possessing a temperature of less than 15 degrees Celsius. The term "cold water" shall, more particularly, mean water possessing a temperature of from zero to 10° C. The term "cold water" shall, still more particularly, mean water possessing a temperature of from zero to 4° C.

The term "dispersant" or "dispersing agent" as used herein connotes a surface-active agent which is added to suspending media to promote uniform suspension or separation of typically extremely fine solid particles, often of colloidal size. Dispersants suitable for purposes of our invention are listed in *McCutcheon's Functional Materials*, at pages 122–142 of the North American Edition (1994), as well as in *McCutcheon's Functional Materials*, at pages 47–56 of the International Edition (1994), both published by MC Publishing Company (McCutcheon Division) of Glen Rock, N.J. In this regard, suitable dispersants include but are not limited to nonionic block copolymers, 46% tetramethyl decynediol on amorphous silica, anionic lignin surfactant formulations (including sodium salts of modified sulfonated lignin; and sodium salts of highly sulfonated lignin), polyvinyl pyrrolidone, sodium butyl naphthalene sulfonate (including diisobutyl sodium sulfosuccinate), dihexyl sodium sulfosuccinate, dioctyl ester of sodium sulfosuccinic acid (including dioctyl sodium sulfosuccinate), ditridecyl sodium sulfosuccinate, sodium dicyclohexyl sulfosuccinate, sodium dodecylbenzene sulfonate, polycarboxylate, sodium salt of polymeric carboxylic acid, polycarboxylate copolymers (including sodium salts of polymers made from the copolymerization of acrylic acid and maleic acid), polyacrylates (including anionic polyacrylate polymer such as polyacrylic acids and sodium polyacrylate), ammonium salt of polyacrylic acid, sodium alkyl naphthalene sulfonates (including sodium di-n-butyl naphthalene sulfonate and sodium di-isopropyl naphthalene sulfonate), lignosulfonates (including nonionic surfactant and sodium lignosulfonate blend; and anionic surfactant and sodium lignosulfonate blend), modified lignosulfonates, sodium and calcium lignosulfonates (including modified calcium lignosulfonate; modified sodium lignosulfonate; modified sodium-calcium lignosulfonate; highly purified calcium lignosulfonate; highly purified sodium lignosulfonate; highly purified partially desulfonated sodium lignosulfonate; sugar-free calcium and sugar-free sodium lignosulfonate; alkaline sugar-free sodium lignosulfonate; and the sodium salt of highly sulfonated kraft pine lignosulfonate), ammonium lignosulfonate, sugar-free ammonium lignosulfonate, sodium polynaphthalene sulfonate, sodium naphthalene sulfonic acid formaldehyde, sodium and calcium salts of polymerized substituted benzoid alkyl sulfonic acids, sodium neutralized condensed naphthalene sulfonic acids (including sodium salts of condensed naphthalene sulfonic acid and sodium salts of a condensed mononaphthalene sulfonic acid), ammonium salts of a condensed mononaphthalene sulfonic acid, sodium salts of polymerized alkyl naphthalene sulfonic acids, potassium salts of polymerized alkyl naphthalene sulfonic acids, calcium salts of polymerized alkyl substituted benzoid alkyl sulfonic acids, sodium salts of polymerized alkyl and substituted benzoid alkyl sulfonic acids, sodium salts of carboxylated polyelectrolytes, sulfonates of condensed naphthalenes, and neutralized sulfonates of naphthalene/formaldehyde condensates (including sodium sulfonates of naphthalene formaldehyde condensate and sodium salts of a sulfonated naphthalene formaldehyde condensate).

The term "dye" as used herein connotes an organic colorant, derived from a petroleum-based intermediate, to impart permanent color to a substrate.

The term "film" as used herein connotes either a veneer; or a relatively fine or thin skin; or a delicate coating on a surface; or an outer membrane; or an ultrafine layer on a substrate.

The term "foam-control" agent or ingredient shall be understood to mean a substance that is used to reduce foaming. Foaming may result from the presence of such foam-inducing agents as proteins, gases, or nitrogenous materials. The presence of foam is generally undesirable because foam may interfere with processing. Foam-control agents are generally discussed at pages 430–447 in the *Kirk-Othmer Encyclopedia of Chemical Technology*, third edition, volume 7, published 1979 by John Wiley & Sons, Inc. Examples of conventional "foam-control" agents include but are not limited to the group consisting of certain organic phosphates, certain silicone fluids, certain sulfonated oils, and 2-octanol.

The term "paste" shall be understood to mean a finely-divided resinous composition, which typically includes a plasticizer-like ingredient to form a fluid or semifluid mixture, wherein the paste is made without use of low boiling solvents or water emulsions.

The term "pigment," which includes the term "dye," as used herein means a composition-of-matter, usually in the form of a dry powder, which imparts color to another composition-of-matter or to a mixture.

The term "room temperature" shall be understood to mean a temperature of from 23 degrees Celsius to 25° C.

The term "sticker" as used herein shall in general be understood to mean an "adherent" or "adhesion agent," the terms "adherent" and "adhesion agent" connoting ingredients capable of causing a substance to adhere to a substrate. In this regard, the "sticker" functions as a carrier.

The term "surfactant"—which includes the terms "emulsifier" and "detergent"—as used herein means a composition-of-matter which either alters surface tension when dissolved in water or an aqueous solution or alters interfacial tension between immiscible liquids or a liquid and a solid. Ssurfactants suitable for purposes of our present invention are listed in *McCutcheon's Emulsifiers & Detergents*, at pages 287–310 of the North American Edition (1994), and in *McCutcheon's Emulsifiers & Detergents*, at pages 257–278 and 280 of the International Edition (1994), both published by MC Publishing Co. (McCutcheon Division) of Glen Rock, N.J. In this regard, suitable surfactants include but are not limited to alkylaryl sulfonates, block polymers, carboxylated alcohol or alkylphenol ethoxylates, ethoxylated alcohols, ethoxylated alkylphenols, glycol esters, lignin & lignin derivatives, polyethylene glycols, silicone-based surfactants, sulfates & sulfonates ethoxylated alkylphenols, sulfonates of condensed naphthalenes, sulfonates of dodecyl and tridecylbenzenes, sulfonates of naphthalene and alkyl naphthalene, sulfosuccinamates, and sulfosuccinates & sulfosuccinate derivatives.

The term "warm water" shall be understood to mean water possessing a temperature which is greater than room temperature.

DETAILED DESCRIPTION OF EXAMPLES

The following examples are set forth to describe more particularly, to those skilled in the art, the principles and practice of our invention. In this regard the examples are not intended to limit our invention. Rather, the examples are intended to be merely illustrative of certain aspects of our various preferred embodiments.

In the following examples there are presented paste formulations which include at least one active ingredient, a hydrocarbon oil carrier having a boiling point of at least 150° C., wherein the carrier is present in an amount that is effective for reducing dusting of a plant leaf or seed, a surfactant, and an effervescent comprising an alkaline carbonate and a solid and weak acid, wherein the surfactant, the alkaline carbonate, and the solid and weak acid are respectively present in an amount that is effective for enabling the paste formulation to readily and quickly be dispersed in water, such as room temperature water, but especially in cold water.

PROCESSING INSTRUCTIONS

All powdered (dry) ingredients, with the exception of low-melting ingredients (below 50° C.) and pigment, were combined in a commercially available ribbon blender and processed for approximately 15 minutes.

The processed mixture was then passed through a "hammermill" type grinder, first through a 0.250-inch (0.635-centimeter) screen, and next through a 0.013-inch (0.033-centimeter) screen, to facilitate reduction of particle size.

The resultant mixture was then blended with the remaining dry ingredients (i.e. the "low-melting" ingredients and the pigment), and blended for approximately 15 minutes.

Thereafter, along with the thus-blended resultant mixture, all liquid ingredients were combined in a mixing vessel and mixed until a homogeneous mixture was obtained.

In the following example(s), ingredients selected should be dry and not contain any so-called "free" water or any other solvent which—if otherwise present—could deleteriously affect the water-soluble bag or pouch in which the paste formulation of the invention is contained.

EXAMPLE 1

One Such Paste Formulation Made With Dry Effervescent

In this example, the processing instructions set forth above were followed, and the ingredients which were utilized are set forth in Table I.

TABLE I

| Ingredients | Weight Percent |
| --- | --- |
| Active | 56.701 |
| Sticker/Carrier | 22.993 |
| Surfactant | 4.000 |
| Solid & Weak Acid | 3.840 |
| Alkaline Carbonate | 3.600 |
| Pigment | 2.500 |
| Anticaking Agent | 1.000 |
| Dispersant No. 1 | 1.000 |
| Dispersant No. 2 | 1.000 |
| Dispersant No. 3 | 1.000 |
| Dispersant No. 4 | 1.000 |
| Dispersant No. 5 | 0.500 |
| Packaging Film | 0.466 |
| Foam-Control Agent | 0.400 |

In Table I (above) the active ingredient, commercially-available from Uniroyal Chemical Company, Inc., of Middlebury, Conn. (U.S.A.), is 5,6-dihydro-2-methyl-N-phenyl-1,4-oxathiin-3-carboxanilide, also known as Vitavax® (97%) or as carboxin, carboxine or carbathiin (its common names). The active ingredient is present in an amount of from 0.1 to 80 weight per cent ("wt. %"), preferably 1 to 60 wt. %.

In Table I the "sticker"/carrier ingredient, a hydrocarbon oil having a boiling point of >315° C., is commercially-available from Shell Chemical Co. of Houston, Tex. The "sticker"/carrier ingredient is present in an amount of from 10 to 50 wt. %, preferably 20 to 40 wt. %.

In Table I the surfactant ingredient, a blend of an anionic oil-soluble sulfonate and a non-ionic polyethylene ether, is commercially-available from Witco Chemical Corp. of New York, N.Y. The surfactant ingredient is present in an amount of from 0.1 to 20 wt. %, preferably 1 to 10 wt. %.

In Table I the (1) solid and weak acid (namely, citric acid, which is an acid in powder form) as well as the (2) alkaline carbonate (namely, sodium carbonate, which is a carbonic source), which together comprise the dry effervescent ingredient, are both commercially-available from Van Water & Rogers, Ltd. of Toronto, Ontario, Canada. Citric acid is present in an amount of 0.1 to 40 wt. %, preferably 1 to 20 wt. %. $Na_2CO_3$ is present in an amount of from 0.1 to 40 wt. %, preferably 1 to 20 wt. %.

In Table I the pigment, 2-naphthalenecarboxylic acid, 3-hydroxy-4-[(4-methyl-2-sulfonphenyl)azo]-calcium salt, is commercially-available from Hoechst of Willowdale, Ontario, Canada. The pigment, an optional ingredient, is present from zero to 30 wt. %, preferably zero to 21 wt. %.

In Table I the anticaking agent or ingredient—amorphous, fumed silicone dioxide—is commercially-available from Cabot Corp. of Boston, Mass. The anticaking ingredient, also an optional ingredient, is present from zero to 20 wt. %, preferably 0. 1 to 5 wt. %.

In Table I dispersant No. 1, a sodium naphthalene sulfonic acid formaldehyde, is commercially-available from R.T. Vanderbilt Co., Inc. of Norwalk, Conn. The dispersant is present in an amount of from 0.1 to 30 wt. %, preferably 0.1 to 10 wt. %.

In Table I dispersant No. 2, a polyoxypropylene-polyoxyethylene block polymer, is commercially-available from BASF Wyandotte Corp. of Parsippany, N.J. The dispersant is present in an amount of from 0.1 to 30 wt. %, preferably 0.1 to 10 wt. %.

In Table I dispersant No. 3, a sodium dodecylbenzene sulfonate, is commercially-available from Stepan Chemical Co. of Northfield, Ill. The dispersant is present in an amount of from 0.1 to 30 wt. %, preferably 0.1 to 10 wt. %.

In Table I dispersant No. 4, a sodium salt of condensed naphthalene sulfonic acid, is commercially-available from the Rohm & Haas Co. of Philadelphia, Pa. The dispersant is present in an amount of from 0.1 to 30 wt. %, preferably 0.1 to 10 wt. %.

In Table I dispersant No. 5, sodium polymethacrylate, is commercially-available from Hamshire Chem. Corp. of Lexington, Mass. The dispersant is present in an amount of from 0.1 to 30 wt. %, preferably 0.1 to 10 wt. %.

In Table I the water-soluble film for packaging, a polymer of predominantly vinyl alcohol, is commercially-available from Specialty Products of McAdoo, Pa. The packaging-film ingredient, also optional, is present in an amount of from 0.1 to 4 wt. %, preferably 0.3to 1 wt. %.

In Table I, the foam-control agent, a blend of emulsifiable mineral oils and silica derivatives, is commercially-available from Drew Chemical Corp. of Boonton, N.J. The foam-control agent is present in an amount of from 0.1 to 20 wt. %, preferably 0.1 to 5 wt. %.

EXAMPLE 2

Another Paste Formulation Made With Dry Effervescent

In this example, the processing instructions set forth above were followed, and the ingredients which were utilized are set forth in Table II.

TABLE II

| Ingredients | Weight Percent |
| --- | --- |
| Active | 56.70 |
| Sticker/Carrier | 22.99 |
| Surfactant | 4.00 |
| Citric Acid | 3.84 |
| Sodium Carbonate | 3.60 |
| Pigment | 2.50 |
| Anticaking Agent | 1.00 |
| Dispersant No. 1 | 1.00 |
| Dispersant No. 2 | 1.00 |
| Dispersant No. 3 | 1.00 |
| Dispersant No. 4 | 1.00 |
| Dispersant No. 5 | 0.50 |
| Foam-Control Agent | 0.40 |

The ingredients listed in Table II are described above in connection with Example 1. Example 2 was prepared following the procedures of Example 1, except that Example 2 did not include packaging film.

EXAMPLE 3

Another Paste Formulation Made With Dry Effervescent

In this example, the processing instructions set forth above were followed, and the ingredients which were utilized are set forth in Table III.

TABLE III

| Ingredients | Weight Percent |
| --- | --- |
| Active | 30.65 |
| Potassium Carbonate | 25.00 |
| Sticker/Carrier | 18.25 |
| Citric Acid | 17.50 |
| Surfactant | 3.00 |
| Pigment | 1.35 |
| Dispersant No. 1 | 1.00 |
| Dispersant No. 2 | 1.00 |
| Dispersant No. 4 | 1.00 |
| Foam-Control Agent | 0.50 |
| Dispersant No. 5 | 0.40 |

The ingredients listed in Table III are described above in connection with Example 1. Example 3 was prepared generally in accordance with the procedures of Examples 1 and 2 except for the following: Potassium carbonate at 25.00% (Example 3) was substituted for sodium carbonate at 3.60% (Examples 1 and 2) as an alkaline carbonate; hydrocarbon oil sticker/carrier weight percentage was less in Example 3 than in Examples 1 and 2; citric acid (solid and weak acid) weight percentage was greater in Example 3 than in Examples 1 and 2; and Example 3 did not include anticaking agent, dispersant No. 3, nor packaging film.

EXAMPLE 4

Another Paste Formulation Made With Dry Effervescent

In this example, the processing instructions set forth above were followed, and the ingredients which were utilized are set forth in Table IV.

TABLE IV

| Ingredients | Weight Percent |
| --- | --- |
| Active | 40.50 |
| Potassium Carbonate | 20.00 |
| Citric Acid | 15.36 |
| Sticker/Carrier | 15.27 |
| Surfactant | 3.00 |
| Pigment | 1.78 |
| Dispersant No. 1 | 1.00 |
| Dispersant No. 2 | 1.00 |
| Dispersant No. 4 | 1.00 |
| Dispersant No. 5 | 0.40 |
| Foam-Control Agent | 0.30 |

The ingredients listed in Table IV are described above in connection with Example 1. Example 4 was prepared generally in accordance with the procedures of Examples 1 and 2 except for the following: Potassium carbonate at 20.00% (Example 4) was substituted for sodium carbonate at 3.60% (Examples 1 and 2) as an alkaline carbonate; hydrocarbon oil sticker/carrier weight percentage was less in Example 4 than in Examples 1 and 2; citric acid (solid and weak acid) weight percentage was greater in Example 4 than in Examples 1 and 2; and Example 4 did not include anticaking agent, dispersant No. 3, nor packaging film.

EXAMPLE 5

Another Paste Formulation Made With Dry Effervescent

In this example, the processing instructions set forth above were followed, and the ingredients which were utilized are set forth in Table V.

TABLE V

| Ingredients | Weight Percent |
| --- | --- |
| Sticker/Carrier | 40.00 |
| Sodium Bicarbonate | 18.00 |
| Pigment | 10.00 |
| Surfactant | 10.00 |
| Tartaric Acid | 7.00 |
| Active | 6.19 |
| Dispersant No. 6 | 4.14 |
| Dispersant No. 1 | 2.00 |
| Dispersant No. 5 | 1.00 |
| Anticaking Agent | 0.50 |
| Foam-Control Agent | 0.40 |

Example 5 was prepared generally in accordance with the procedures of Example 1 except for the following: The active ingredient is α-[2-(4-chlorophenyl)ethyl]-α-(1,1-dimethylethyl)-1H-1,2,4-triazole-1-ethanol, also known as tebuconazole (common name); tartaric acid was substituted for citric acid as a solid and weak acid; sodium bicarbonate was substituted for sodium carbonate and potassium carbonate as an alkaline carbonate; hydrocarbon oil sticker/carrier weight percentage was greater in Example 5 than in Example 1; Example 5 included formulated polyoxyethylene, polyoxypropylene block copolymer (dispersant No. 6), available from BASF Corp. of Parsippany, N.J.; and Example 5 did not include dispersants Nos. 2–4, nor packaging film.

EXAMPLE 6

Another Paste Formulation Made With Dry Effervescent

In this example, the processing instructions set forth above in Example 1 were followed, and the ingredients which were utilized are set forth in Table VI.

TABLE VI

| Ingredients | Weight Percent |
| --- | --- |
| Active | 56.70 |
| Sticker/Carrier | 23.00 |
| Surfactant | 4.00 |
| Citric Acid | 3.85 |
| Sodium Carbonate | 3.60 |
| Pigment | 2.50 |
| Dispersant No. 4 | 2.00 |
| Anticaking Agent | 1.00 |
| Dispersant No. 2 | 1.00 |
| Dispersant No. 3 | 1.00 |
| Dispersant No. 5 | 1.00 |
| Foam-Control Agent | 0.35 |

The ingredients listed in Table VI are described above in connection with Example 2. Example 6 was prepared substantially following the procedures of Example 2, except that Example 6 did not include the sodium naphthalene sulfonic acid formaldehyde (dispersant No. 1) of Example 2, and the fomulation of Example 6 used refined canola oil (a vegetable oil) in lieu of the hydrocarbon oil of Example 2.

EXAMPLE 7

Another Paste Formulation Made With Dry Effervescent

In this example, the processing instructions set forth above in Example 5 were followed, and the ingredients which were utilized are set forth in Table VII.

TABLE VII

| Ingredients | Weight Percent |
| --- | --- |
| Sticker/Carrier | 40.00 |
| Pigment | 20.83 |
| Active | 12.89 |
| Surfactant | 10.00 |
| Citric Acid | 7.78 |
| Sodium Carbonate | 7.50 |
| Anticaking Agent | 0.50 |
| Foam-Control Agent | 0.50 |

Example 7 was prepared generally in accordance with the procedures of Example 5, except that citric acid and sodium carbonate were used (Example 7) in lieu of tartaric acid and sodium bicarbonate (Example 5), respectively, and the formulation of Example 7 contained no dispersant.

EXAMPLE 8

Paste Formulation Useful For Foliar Treatment

In this example, the processing instructions set forth above in connection with Example 2 were followed, and the ingredients which were utilized are set forth in Table VIII.

TABLE VIII

| Ingredient | Weight Percent |
| --- | --- |
| Active | 30.85 |
| Sticker/Carrier | 30.00 |
| Surfactant | 22.85 |
| Citric Acid | 3.85 |
| Sodium Carbonate | 3.60 |
| Pigment | 2.50 |
| Dispersant No. 4 | 2.00 |
| Anticaking Agent | 1.00 |
| Dispersant No. 2 | 1.00 |
| Dispersant No. 3 | 1.00 |
| Dispersant No. 5 | 1.00 |

The ingredients listed in Table VIII are described above in connection with Example 2, except as follows.

Example 8 was prepared substantially following the procedures of Example 2, except that Example 8 did not include foam-control agent, nor did Example 8 contain dispersant No. 1; and the active used in Example 8 was (±)-tetrahydrofurfuryl(R)-2-[4-(6-chloroquinoxalin-2-yloxy) phenoxy] propanate, also known as Pantera™ (95%) and commercially-available from Uniroyal Chemical Company, Inc.

RESULTS

The above-described pastes were easily let down in water and the resultant aqueous suspensions, except for Example 8, were used to coat seeds of sceptre durum wheat. The thus-coated seeds were observed to be smooth, shiny and dyed evenly red. Dustiness of the coated seeds was measured by known light-scattering methods.

Table IX presents data showing the amount of dust generated from grams of seed by each seed treatment vis-a-vis an untreated sample.

TABLE IX

| Type of Seed Treatment | Dust Generated ($mg/m^3$) |
| --- | --- |
| Untreated | 1.50 |
| Composition Of Example 2 | 0.44 |
| Composition Of Example 3 | 0.19 |
| Composition Of Example 5 | 0.26 |
| Composition Of Example 6 | 0.40 |
| Composition Of Example 7 | 0.37 |

PRESENCE OF EFFERVESCENT SALTS

The presence of effervescent salt facilitates considerably the dispersion of the paste in water, as is demonstrated by the following.

TABLE X

| Paste Made | $H_2O$ Temperature | Dispersion Time |
| --- | --- | --- |
| With Effervescent Salt | 20° C. | 2.5 minutes |
| | 5° C. | 3 minutes |
| Without Effervescent Salt | 20° C. | 12 minutes |
| | 5° C. | 25 minutes |

DISPERSION TESTING PROCEDURES

The presence of effervescent salt as well as the absence of effervescent salt, as exemplified by considering the dispersion of paste formulations in water at 20° C. and at 5° C., was investigated as follows.

A Gyrotory Shaker (Model G2 from New Brunswick Scientific Co. Inc.), set at 200 revolutions per minute was used.

A sample of paste (10 grams of formulation in 70 grams of water), with effervescent (i.e. including the potassium carbonate and citric acid) identified in Example 3, was compared with a like sample of paste (5.75 grams of formulation in 70 grams of water) without effervescent salt according to the following procedure.

To a 200 milliliter ("ml") beaker, securely mounted on the Gyrotory Shaker, was added a paste sample—as a single "globule." Then water (70 grams at 20° C. or at 5° C.) was added at once. Next, the Gyrotory Shaker was switched "on" to start the circular motion of the beaker. The dispersion was deemed "complete" when no paste was visibly detected in the let-down suspension. This condition (dispersion "completeness") was readily observable whenever the Gyrotory Shaker was switched "off" briefly and the beaker contents decanted into another beaker.

ADDITIONAL INGREDIENTS

Additional actives suitable for purposes of our present invention include 5,6-dihydro-2-methyl-1,4-oxathi-ine-3-carboxanilide 4,4-dioxide also known as oxycarboxin (common name) as well as by its trade name "Plantvax"®; 2,3-dihydro-2,2-dimethyl-7-benzofuranyl methyl carbamate, also known as carbofuran (its common name); methylcarbamic acid 2-(2-chloro-1-methoxy ethoxy) phenyl ester, also known as cloethocarb (its common name); 2-(4-chlorophenyl)-3-cyclopropyl-1-(1H-1,2,4-triazol-1-yl)-butan-2-ol, also known as cyproconazole (its common name); pentachloronitrobenzene, also known as quintozene (common name) as well as by its trade name "Terraclor"; 5-ethoxy-3-(trichloromethyl)-1,2,4-thiadiazole, also known as etridiazole (common name) as well as its trade name "Terrazole"; *Rhizobium sp; Penicillium bilajii; Bacillus subtilis*; β-(4-chlorophenoxy)-α-(1,1-dimethylethyl)-1H-1,2,4-triazole-1-ethanol, also known as triadimenol (common name) or by its trade name "Baytan"; tetramethylthiuram disulfide, also known as thiram (common name); 2-(4-thiazolyl) benzimidazole, also known as thiabendazole (common name) as well as its abbreviation "TBZ"; (2-methyl[1,1'-biphenyl]-3-yl)methyl-3-(2-chloro-3,3,3-trifluoro-1-propenyl)-2,2-dimethylcyclopropane-carboxylate, also known as bifenthrin (common name); 1,2,3,4,5,6-hexachlorocyclo- hexane, gamma-isomer, also known as lindane (common name); N-(2,6-dimethylphenyl)-N-(methoxyacetyl)alanine methyl ester, also known as metalaxyl (common name); 1-[(6-chloro-3-pyridinyl)methyl]-N-nitro-2-imidazolidinimine, also known as imidacloprid (common name); and α-butyl-α'-(4-chlorophenyl)-1H-1,2,4-triazole propanenitrile, also known as myclobutanil (common name).

Additional anticaking agents suitable for purposes of the present invention—in addition to fumed silica (untreated or treated)—include but are not limited to synthetic calcium silicate, sodium polyalkyl naphthalene sulfonate, microcrystalline cellulose, and sodium aluminosilicate.

Additional packaging-film ingredients suitable for purposes of our invention are set forth at pages 207–230 in the *Kirk-Othmer Encyclopedia of Chemical Technology*, third edition, volume 20, published 1982 by John Wiley & Sons, Inc., and at page 232 of *Kirk-Othmer Encyclopedia Of Chemical Technology*, third edition, volume 10, published 1980.

Additional foam-control agents suitable for purposes of our present invention include but are not limited to silicone-based powder (available from Calgene Chemical Inc. of Skokie, Ill.); mineral oil adsorbed onto silica substrate (available from Rhone Poulenc Corp. of Cranbury, N.J.); tallow soap; synthetic oil adsorbed onto hydrophilic silica (available from Ross Chemical of Fountain Inn, S.C.); silica-based powders; silicone defoamer; and various mixtures of silicone, silica, and polyethylene glycol 600 dioleate.

Preferred active ingredients are selected from the group consisting of triadimenol; imidacloprid; lindane; oxycarboxin; tebuconazole; thiabendazole; thiram; carboxin; and mixtures thereof.

Preferred hydrocarbon oil carrier is selected from the group consisting of vegetable oil (such as canola oil), petroleum-based hydrocarbon oil, paraffinic/naphthenic hydrocarbon oil, mineral oil, and mixtures thereof.

Preferred dispersants are selected from the group consisting of block polymers, alkylphenol ethoxylates, ethoxylated alcohols, ethoxylated alkylphenols, polyacrylic acid, propoxylated alkylphenols, sulfonated ethoxylated alkylphenols, lignin & lignin derivatives, tridecyl & dodecyl benzene sulfonic acid, and mixtures thereof.

Preferred packaging-film ingredients include methyl cellulose; polyethylene oxide; polyvinyl alcohol; and starch. (The weight percentage of a film depends upon the desired density and thickness of the film.)

Preferred solid and weak acid ingredients are selected from the group consisting of citric acid, tartaric acid, succinic acid, malic acid, malonic acid, and mixtures thereof.

Preferred alkaline carbonate ingredients are selected from the group consisting of sodium carbonate, potassium carbonate, sodium bicarbonate, potassium bicarbonate, and mixtures thereof.

Preferred surfactants are selected from the group consisting of alkaryl sulfonates, diphenyl sulfonate derivatives, lignin & lignin derivatives, silicone-based surfactants, sulfonates of condensed naphthalenes, sulfonates of dodecyl/tridecyl benzene, sulfonates of naphthalene & alkyl naphthalene, sulfosuccinamates, sulfosuccinates, and mixtures thereof.

DISCLOSED AND DESCRIBED HEREIN

What has been described herein is a water-dispersible paste formulation which is useful for seed treatment and for foliar treatment of plants.

While our invention has been described with reference to a number of preferred embodiments, it is to be understood that the scope of our invention is not to be limited to these preferred embodiments.

On the contrary, alternatives, changes and/or modifications will readily become apparent to those skilled in the art upon reading our foregoing detailed description.

For example, combinations of more than one active ingredient —e.g. fungicide, insecticide, plant growth regulatory agent, and/or biological agent—may be incorporated into the compositions of the present invention.

Accordingly, such alternatives, changes and modifications are to be understood as forming a part of our invention insofar as such fall within the spirit and scope of the claims.

We claim:

1. A dry water-dispersible paste formulation useful for seed treatment and foliar treatment of plants, comprising:
   about 0.1% to about 80% by weight of at least one active ingredient;
   about 10% to 50% by weight of a hydrocarbon oil carrier having a boiling point of at least 150 degrees Celsius;
   about 0.1 to about 20% by weight of a surfactant; and
   about 0.1% to about 40% by weight of an alkaline carbonate and
   about 0.1% to about 40% by weight of a solid and weak acid.

2. The water-dispersible paste formulation of claim 1 further including a foam-control agent.

3. The water-dispersible paste formulation of claim 1 further including about 0.1% to 30% by weight of one or more dispersing agents.

4. The water-dispersible paste formulation of claim 1 wherein the hydrocarbon oil carrier has a boiling point of at least 200 degrees Celsius.

5. The water-dispersible paste formulation of claim 1 wherein the hydrocarbon oil carrier has a boiling point of at least 220 degrees Celsius.

6. The water-dispersible paste formulation of claim 3 wherein the surfactant, the dispersant, the alkaline carbonate, and the solid and weak acid are respectively present in an amount that is effective for enabling the paste formulation to readily and quickly be dispersed in room temperature water.

7. The water-dispersible paste formulation of claim 3 wherein the surfactant, the dispersant, the alkaline carbonate, and the solid and weak acid are respectively present in an amount that is effective for enabling the paste formulation to readily and quickly be dispersed in cold water.

8. The water-dispersible paste formulation of claim 1 further including a pigment ingredient.

9. The water-dispersible paste formulation of claim 1 further including an anticaking ingredient.

10. The water-dispersible paste formulation of claim 1 wherein the solid and weak acid is selected from the group consisting of citric acid, tartaric acid, succinic acid, malic acid, malonic acid, and mixtures thereof.

11. The water-dispersible paste formulation of claim 1 wherein the alkaline carbonate is selected from the group consisting of sodium carbonate, potassium carbonate, sodium bicarbonate, potassium bicarbonate, and mixtures thereof.

12. The water-dispersible paste formulation of claim 1 wherein the surfactant is selected from the group consisting of alkaryl sulfonates, diphenyl sulfonate derivatives, lignin & lignin derivatives, silicone-based surfactants, sulfonates of condensed naphthalenes, sulfonates of dodecyl/tridecyl benzene, sulfonates of naphthalene & alkyl naphthalene, sulfosuccinamates, sulfosuccinates, and mixtures thereof.

13. The water-dispersible paste formulation of claim 3 wherein the dispersant is selected from the group consisting of block polymers, alkylphenol ethoxylates, ethoxylated alcohols, ethoxylated alkylphenols, polyacrylic acid, propoxylated alkylphenols, sulfonated ethoxylated alkylphenols, lignin & lignin derivatives, tridecyl & dodecyl benzene sulfonic acid, and mixtures thereof.

14. The water-dispersible paste formulation of claim 1 wherein the hydrocarbon oil carrier is selected from the group consisting of vegetable oil, petroleum-based hydrocarbon oil, paraffinic/naphthenic hydrocarbon oil, mineral oil, and mixtures thereof.

15. In combination with a water-soluble container, a dry water-dispersible paste formulation contained within the water-soluble container, wherein the water-dispersible paste formulation is useful for seed treatment and foliar treatment of plants, wherein the water-dispersible paste formulation comprises:

about 0.1% to about 80% by weight of at least one active ingredient;

about 10% to 50% by weight of a hydrocarbon oil carrier having a boiling point of at least 150 degrees Celsius;

about 0.1 to about 20% by weight of a surfactant; and about 0.1% to about 40% by weight of an alkaline carbonate and about 0.1% to about 40% by weight of a solid and weak acid.

16. The combination of claim 15 wherein the water-dispersible paste formulation further includes a foam-control agent.

17. The combination of claim 15 wherein the water-dispersible paste formulation further includes about 0.1% to 30% by weight of one or more dispersing agents.

18. The combination of claim 15 wherein the water-dispersible paste formulation further includes an anticaking ingredient.

19. The combination of claim 17 wherein the surfactant, the dispersant, the alkaline carbonate, and the solid and weak acid are respectively present in an amount that is effective for enabling the paste formulation to readily and quickly be dispersed in room temperature water.

20. The combination of claim 17 wherein the surfactant, the dispersant, the alkaline carbonate, and the solid and weak acid are respectively present in an amount that is effective for enabling the paste formulation to readily and quickly be dispersed in cold water.

21. The combination of claim 15 wherein the solid and weak acid is selected from the group consisting of citric acid, tartaric acid, succinic acid, malic acid, malonic acid, and mixtures thereof.

22. The combination of claim 15 wherein the alkaline carbonate is selected from the group consisting of sodium carbonate, potassium carbonate, sodium bicarbonate, potassium bicarbonate, and mixtures thereof.

23. The combination of claim 15 wherein the water-dispersible paste formulation further includes a pigment ingredient.

* * * * *